United States Patent [19]

Wu

[11] Patent Number: 5,279,952
[45] Date of Patent: Jan. 18, 1994

[54] PCR-BASED STRATEGY OF CONSTRUCTING CHIMERIC DNA MOLECULES

[75] Inventor: Kun C. Wu, Omaha, Nebr.

[73] Assignee: Board of Regents, The University of Texas System, Austin, Tex.

[21] Appl. No.: 743,245

[22] Filed: Aug. 9, 1991

[51] Int. Cl.$^5$ ...................... C12N 15/10; C12P 19/34
[52] U.S. Cl. ............................... 435/172.3; 435/91.2; 435/91.41; 935/23
[58] Field of Search ................... 435/91, 320.1, 172.3; 935/23

[56] References Cited

PUBLICATIONS

Jones et al., *Diotechniques*, vol. 8, 1990, pp. 178–183.
Higuchi, "Using PCR to Engineer DNA", in *PCR Technology*, 1990, M. Stockton Press, N.Y., pp. 61–70.
Mole et al., Using the Polymerase Chain Reaction to Modify Expression Plasmids for Epitope Mapping, *Nucleic Acids Research* (1989) vol. 17, No. 8, p. 3319.
Silver and Keerikatte, Novel Use of Polymerase Chain Reaction to Amplify Cellular DNA Adjacent to an Integrated Provirus, *Journal of Virology* (1989) 63:1924–1928.
Triglia et al., A Procedure for In Vitro Amplification of DNA Segments that Lie Outside the Boundaries of Known Sequences, *Nucleic Acids Research* (1988) vol. 16, No. 16, p. 8186.
Wilson et al., Expression Vector pT7: TKII for the Synthesis of Authentic Biologically Active RNA Encoding Vaccinia Virus Thymidine Kinase, 1989, Oregon Agricultural Experiment Station Technical Paper No. 8734, pp. 69–78.
Orlandi et al., Cloning Immunoglobulin Variable Domains for Expression by the Polymerase Chain Reaction, *Proc. Natl. Acad. Sci.*, (1989) pp. 3833–3837.
Horton et al., Engineering Hybrid Genes Without the Use of Restriction Enzymes: Gene Splicing by Overlap Extension, *Gene* (1989) 77:61–68.
Abbot et al., The Gene for Human Complement Component C9 Mapped to Chromosome 5 by Polymerase Chain Reaction, *Genomics* 4, (1989) pp. 606–609.
Pratt et al., Ig V Region Gene Expression in Small Lymphocytic Lymphoma with Little or No Somatic Hypermutation, *Journal of Immunology*, (Jul. 1989), vol. 143, No. 2, pp. 699–705.
Carroll et al., Absence of Ig V Region Gene Somatic Hypermutation in Advanced Burkitt's Lymphoma, *Journal of Immunology* (Jul. 1989) vol. 143, No. 2, pp. 692–698.
Oste et al., Polymerase Chain Reaction, *BioTechniques* (1988) vol. 6, No. 2, pp. 162–167.
Vallette et al., Construction of Mutant and Chimeric Genes Using the Polymerase Chain Reaction, *Nucleic Acids Research* (1989) vol. 17, pp. 723–733.
Syvänen et al., Quantification of Polymerase Chain Reaction Products by Affinity-Based Hybrid Collection, *Nucleic Acids Research* (1988) 16:11327–11338.
Shuldiner et al., Hybrid DNA Artifact from PCR of Closely Related Target Sequences. *Nucleic Acids Research* (1989) 11:4409.
Morgan et al., Polymerase Chain Reaction for Detection of Residual Leukaemia *The Lancet* (1989) pp. 928–929.

*Primary Examiner*—Richard A. Schwartz
*Assistant Examiner*—James Ketter
*Attorney, Agent, or Firm*—Arnold White & Durkee

[57] ABSTRACT

The invention relates to methods for the use of the polymerase chain reaction to amplify a segment of a cloned gene of interest in such a way as to allow a simplified introduction of alterations such as deletions, insertions, repetitions (both direct and inverted) and substitutions into the cloned gene in a specific and precise manner. The unique, amplified segment of the cloned gene so amplified is a common substrate for each of the different approaches to introducing the various alterations into the gene. Choice of the primer sites within the amplified segment coupled with choice of the orientation of the molecule once ligated to itself results in the various resulting embodiments of the invention.

14 Claims, 9 Drawing Sheets

1. Insertion of cloned fragment into vector and amplification:
   (vector DNA)---EcoRI..... A  B  C ..... EcoRI--(vector DNA)

2. Restriction of vector DNA containing cloned fragment:
   EcoRI..... A  B  C ..... EcoRI 3. Ligation of restriction fragment to itself, head-to-tail:
   EcoRI..... A B C ..... EcoRI ..... A B C ..... EcoRI 4. Initiation of polymerase chain reaction at primer sites:
   EcoRI..... A B <u>C.....</u>> .. EcoRI ..<<u>.....A</u> B C ..... EcoRI 5. Purification of PCR-generated fragment missing target site:
   C ..... EcoRI ..... A 6. Ligation of deletion fragment to itself, head-to-tail:
   C..... EcoRI..... A    C..... EcoRI..... A 7. Restriction of ligated deletion fragment:
   EcoRI..... A    C..... EcoRI 8. Reinsertion of deletion fragment into expression vector:
   (vector DNA)---EcoRI..... A    C..... EcoRI---(vector DNA)

Fig. 1

1. Insertion of cloned fragment into vector and amplification:
   (vector DNA)---EcoRI . . . . . A  B  C . . . . . EcoRI---(vector DNA)

2. Restriction of vector DNA containing cloned fragment:
   EcoRI . . . . . A  B  C . . . . . EcoRI 3. Ligation of restriction fragment to itself, head-to-tail:
   EcoRI . . . . . A  B  C . . . . . EcoRI . . . . . A  B  C . . . . . EcoRI 4. Initiation of polymerase chain reaction at primer sites:
   EcoRI . . . . . A  B  C̲ ̲ ̲ ̲₎ . . EcoRI . . ₍ ̲ ̲ ̲ ̲A  B  C . . . . . EcoRI 5. Purification of PCR-generated fragment missing target site:
   C . . . . . EcoRI . . . . . A 6. Ligation of deletion fragment to the chimeric DNA sequence and to itself, head-to-tail:
   C . . . . . EcoRI . . . . . A  B' C . . . . . EcoRI . . . . . A 7. Restriction of ligated chimeric fragment:
   EcoRI . . . . . A  B' C . . . . . EcoRI 8. Reinsertion of chimeric fragment into expression vector:
   (vector DNA)---EcoRI . . . . . A  B' C . . . . . EcoRI---(vector DNA)

Fig. 2

1. Insertion of cloned fragment into vector and amplification:
   (vector DNA) --- EcoRI . . . 123456789 . . . EcoRI --- (vector DNA).

2. Restriction of vector DNA containing cloned fragment:
   EcoRI . . . 123456789 . . . EcoRI.

3. Ligation of restriction fragment to itself, head-to-tail:
   EcoRI . . . 123456789 . . .EcoRI . . . 123456789 . . . EcoRI 4. Initiation of polymerase chain reaction at primer sites:
   EcoRI . . . 1234<u>567</u>>89 . . EcoRI . . 12<<u>3456</u>789 . . . EcoRI 5. Purification of fragment with two copies of sequence 5:
   56789 . . . . . EcoRI . . . . . 12345.

6. Ligation of fragment containing two copies of sequence 5 to itself, head-to-tail:
   56789 . . . . . EcoRI . . . . . 1234556789 . . . . . EcoRI . . . . .12345

7. Restriction of ligated fragment containing sequence 5 directly repeated:
   EcoRI . . . 1234556789 . . . EcoRI 8. Reinsertion of fragment containing sequence 5 directly repeated into vector:
   (vector DNA) --- EcoRI . . . 1234556789 . . . EcoRI --- (vector DNA).

Fig. 3

1. Insertion of cloned fragment into vector and amplification:
   (vector DNA) --- EcoRI . . . 123456789 . . . EcoRI --- (vector DNA).

2. Restriction of vector DNA containing cloned fragment:
   EcoRI . . . 123456789 . . . EcoRI.

3. Ligation of restriction fragment to itself, tail-to-tail:
   EcoRI . . . 123456789 . . . EcoRI . . . 987654321 . . . EcoRI.

4. Initiation of polymerase chain reaction at primer sites:
   EcoRI . . . 12345<u>678</u>>9 . . EcoRI . . 9<<u>876</u>54321 . . . EcoRI 5. Purification of fragment with two copies of sequence 6789:
   6789 . . . . . EcoRI . . . . . 9876

6. Ligation of fragment containing two copies of sequence 6789 to itself, head-to-tail:
   6789 . . . . . EcoRI . . . . . 98766789 . . . . . EcoRI . . . . . 9876

7. Restriction of ligated fragment containing sequence 6789 repeated in inverted fashion:
   EcoRI . . . 98766789 . . . EcoRI 8. Reinsertion of fragment containing sequence 6789 repeated in inverted fashion into vector:
   (vector DNA) --- EcoRI . . . 98766789 . . . EcoRI --- (vector DNA).

Fig. 4

| OLIGONUCLEOTIDE | LOCATION 5' TO ZETA CAP |
|---|---|
| I | -302 to -270 |
| II | -249 to -267 |
| III | -203 to -226 |
| IV | -178 to -216 |
| V | -149 to -187 |
| VI | -110 to -145 |
| VII | -93 to -109 |
| VIII | -65 to -92 |
| IX | 0 to -23 |

THIS AREA ACTIVATES GLOBIN PROMOTER

The MST II (-391) - MST II (-132) Fragment has been shown to activate a beta globin promoter in K562.

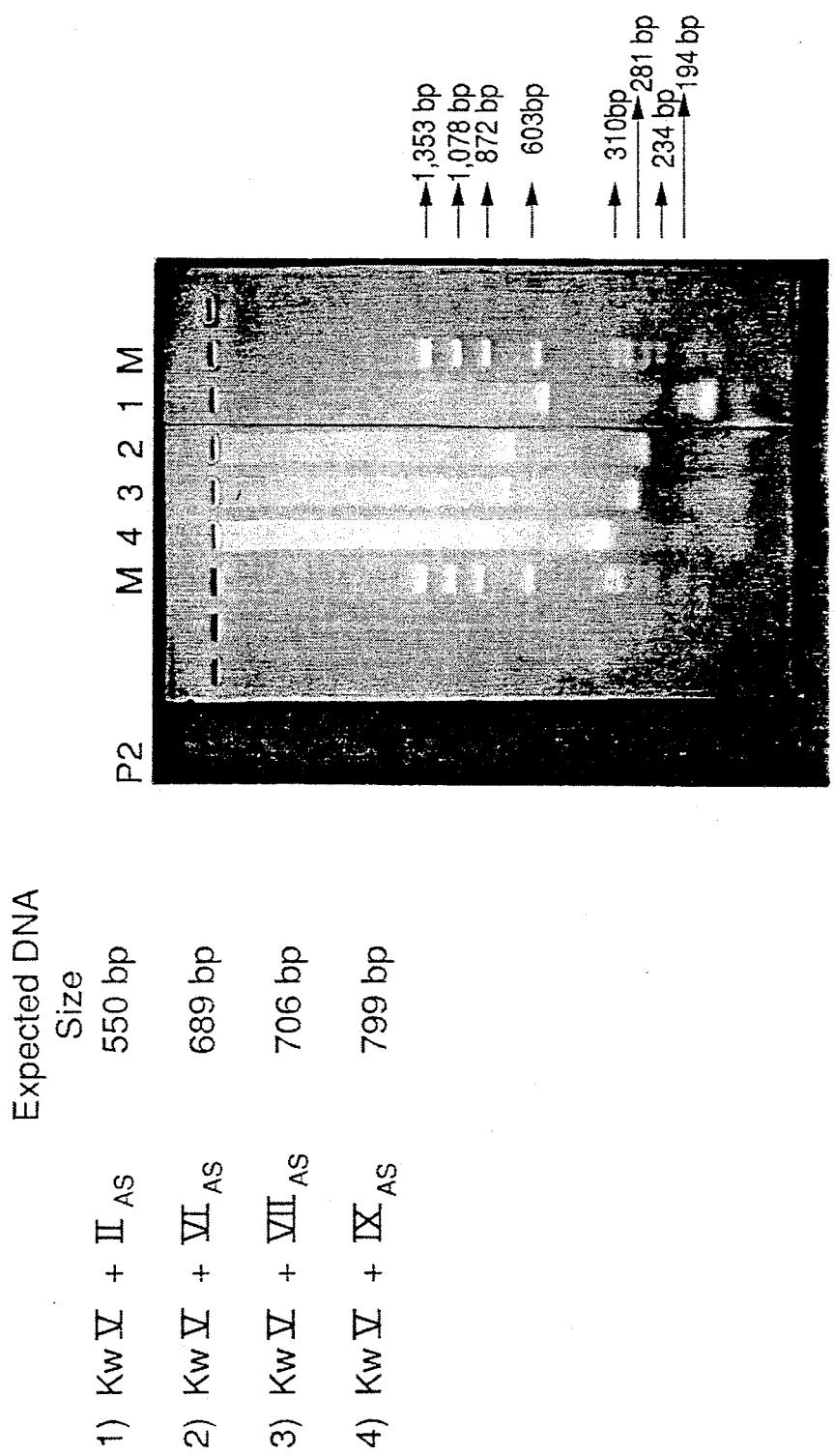

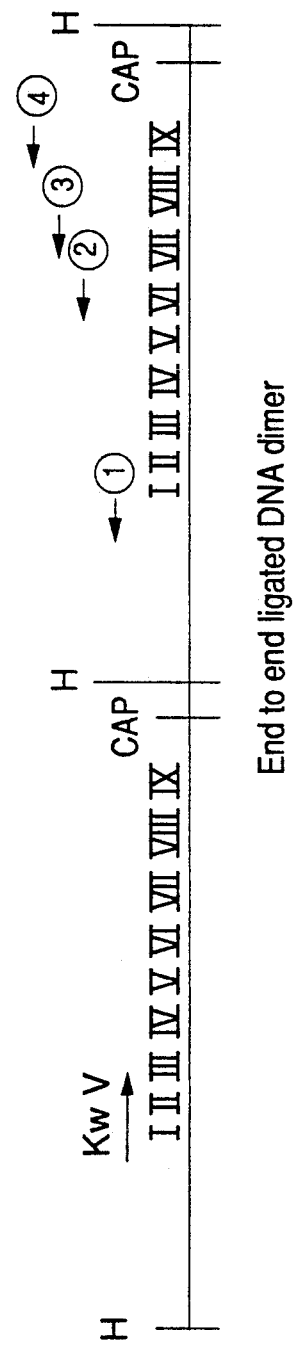

PCR-BASED STRATEGY OF CONSTRUCTING CHIMERIC DNA MOLECULES

BACKGROUND OF THE INVENTION

1. Field of the Invention

The present invention relates to the construction of altered DNA molecules utilizing polymerase chain reaction. The alteration may involve insertion, deletion, repetition (both direct and inverted), or substitution of DNA sequences with a high degree of precision and may be accomplished in certain instances for alterations as small as a single base pair. The invention relates as well to the construction of chimeric DNA molecules.

2. Description of the Related Art

The polymerase chain reaction (PCR) technique was conceived and developed by the Cetus Corporation to provide for specific amplification of discrete fragments of DNA in order to allow simplified detection and purification of nucleic acid fragments initially present in a particular sample in only picogram quantities (Saiki, et al., *Science* 230:1350-1354, 1985). The procedure mimics the natural DNA replication process in that the number of DNA molecules generated doubles after each cycle. The basic method is based on the repetition of three steps, all conducted in a successive fashion under controlled temperature conditions: (1) denaturing the double-stranded template DNA; (2) annealing the single-stranded primers to the complementary single-stranded regions on the template DNA; and, (3) synthesizing additional DNA along the templates by extension of the primer DNAs with DNA polymerase. After 4 to 25 cycles of these steps, as much as a $10^5$-fold increase in the original DNA is observed (Oste, *BioTechniques* 6:162-167, 1988).

Initially, the PCR technique was used primarily in cloning and sequencing applications. More recently, PCR technology has been used for mutagenesis of specific DNA sequences and for other directed manipulations of DNA.

For instance, PCR technology has been used to engineer hybrid (chimeric) genes without the need to use restriction enzymes in order to segment the gene prior to hybrid formation. In this approach, fragments of the different genes that are to form the hybrid are generated in separate polymerase chain reactions. The primers used in these separate reactions are designed so that the ends of the different products of the separate reactions contain complementary sequences. When these separately produced PCR products are mixed, denatured and reannealed, the strands having matching sequences at their 3'-ends overlap and act as primers for each other. Extension of this overlap by DNA polymerase produces a molecule in which the original sequences are spliced together to form the hybrid gene. Thus, this method requires four primers to construct a deleted, hybrid DNA molecule. Likewise, the method requires six primers and three rounds of PCR in order to construct a chimeric molecule. Furthermore, it does not allow a straightforward means to generate inverted or directly repeated DNA sequences (Horton, et al., *Gene* 77:61-68, 1989).

Since the primer regions used for PCR need not match the template gene sequence exactly, it has been possible to incorporate restriction sites within the primers (Scharf, et al., *Science* 233:1076-1078, 1986). A recent application of this approach involved the cloning and expression of immunoglobulin V genes (Orlandi, et al., *Proc.Natl.Acad.Sci.* 86:3833-3837, 1989). In this application of PCR technology, use was made of the conserved regions at each end of the nucleotide sequences encoding the V domains of mouse immunoglobulin heavy chain ($V_H$) and light chain ($V_K$). Primers were designed for PCR amplification which incorporated restriction sites and which, thereby, mutated the PCR-generated fragments to allow for ease in subcloning the amplified regions into appropriate expression vectors.

In other applications, it was possible to vary the standard PCR approach (which requires oligonucleotide primers complementary to both ends of the segment to be amplified) to allow amplification of DNA flanked on only one side by a region of known DNA sequence (Silver and Keerikatte, *J.Virol.* 63:1924-1928, 1989). This technique requires the presence of a known restriction site within the known DNA sequence and a similar site within the unknown flanking DNA sequence which is to be amplified. After restriction and recircularization, the recircularized fragment is restricted at an unique site between the two primers and the resulting linearized fragment is used as a template for PCR amplification.

Another approach which allows the amplification of unknown sequences of DNA was developed by Triglia, et al. (*Nucl.Acids Res.* 16:8186, 1988). The approach requires the inversion of the sequence of interest by circularization and re-opening at a site distinct from the one of interest, and is called "inverted PCR." A fragment is first created in which two unknown sequences flank on either side a region of known DNA sequence. The fragment is then circularized and cleaved with an unique restriction endonuclease which only cuts within the known DNA sequence creating a new fragment containing all of the DNA of the original fragment but which is then inverted with regions of known sequence flanking the region of unknown sequence. This fragment is then utilized as a PCR substrate to amplify the unknown sequence.

Mutant and chimeric genes have also been produced using PCR in a specific approach which involves using a supercoiled plasmid DNA as a template for PCR and a primer bearing some sort of mutated sequence which is incorporated into the amplified product. Using this procedure, a single amino acid replacement, a sixteen amino acid deletion and a twelve amino acid substitution were introduced into the terminal signal sequence of rat hepatic cytochrome P450b (Vallette, et al., *Nucl-.Acids Res.* 17:723-733, 1989). Using the method of this reference DNA sequences may be inserted only at the 5'-end of the DNA molecule which one wishes to alter. In addition, since the inserted sequence is part of the primer and has to be synthesized, the technique is limited to shorter DNA sequences amenable to economical DNA synthesis (synthetic DNAs over 100 bp are very expensive). It is not clear how hybrid or substituted DNA molecules can be constructed by this technique.

In a procedure similar to that of Vallette, et al. (1989), PCR was used to create deletions within existing expression plasmids (Mole, *Nucl.Acids Res.* 17:3319, 1989). This application of PCR technology demonstrated the advantage that the modified region need not be excised from the plasmid. However, PCR was performed around the entire plasmid (containing the fragment to be deleted) from primers whose 5'-ends defined the region to be deleted. Self-ligation of the PCR product recircularized the plasmid. Recircularization required by this method, however, is typically low efficiency and the yield of recircularized DNA is hard to control.

One of the major limitations of PCR technology as currently practiced in the construction of DNA molecules is the error-prone nature of Tag polymerase. Use of Tag polymerase results on average in one mutation per 400 base pairs polymerized per 30 PCR cycles. Thus, the higher the number of cycles used to produce the desired PCR product, the higher the probability of generating unwanted mutations. Such mutations are especially critical where functional DNA products such as protein coding regions or promoter domains are very sensitive to change.

The techniques of the prior art (supra) typically require the introduction of mutated primers or require extensive DNA duplication around the entire length of a plasmid vector in order to introduce deletions, insertions or substitutions into a specific site within a given DNA sequence. Furthermore, certain of the prior art approaches require multiple primers and multiple PCR-treatments in order to achieve the desired alteration. Some of the methods taught by the prior art are limited to alterations at the termini of a DNA molecule and others require inefficient recircularization of the vector carrying the DNA sequence to be altered. Still others are limited by the size of economical synthetic primers. None of the prior art references appear to be readily amenable to generation of repeated sequences within a DNA molecule. A universally applicable method which utilizes the advantages of PCR amplification but which is not limited in the manners outlined above is needed to make PCR-generated DNA alteration a generally useful tool.

SUMMARY OF THE INVENTION

The present invention provides a unique approach which takes advantage of the PCR technique to provide deletions, insertions, repetitions (both direct and inverted) and substitutions into specific sites within a given DNA sequence. This approach does not require the use of either mutated primers nor does it require amplification of the plasmid vector DNA. The methods of the present invention requires a pair of primers and only a single PCR-treatment in order to achieve the desired alteration. The method of the present invention is not limited to alterations at the termini of a DNA molecule and nor does it require inefficient recircularization of the vector carrying the DNA sequence to be altered. The size of the synthetic primers required by the invention fall within the very economical, small range. Thus, the present invention provides a universally applicable method which utilizes the advantages of PCR amplification but which is not limited in the manners outlined supra in order to make PCR-generated DNA alteration a generally useful tool. The present invention provides a method for producing unique fragments which have been amplified by PCR and which exhibit the flexibility to be used as a means for introducing a variety of alterations depending on the subsequent steps taken using these fragments as the principal substrates. These advantages are achieved with minimal requirements for PCR cycles thus eliminating a source of potential mutations in the product.

In certain general embodiments, the invention achieves its general applicability as a method for constructing altered DNA molecules by first obtaining a suitable amount of the cloned segment containing the DNA sequence to be altered. This is achieved by methods known well to those of skill in the art by inserting the cloned segment of DNA into a plasmid vector at a known restriction endonuclease site. The resulting vector will contain the cloned segment of DNA flanked on either of its sides by two new restriction endonuclease sites corresponding to the known restriction site used to generate the cloned segment and also to open the vector prior to insertion.

One practicing the methods of the invention will select a site to be altered within the cloned segment of DNA. Furthermore, one practicing the invention will determine the type of alteration to be achieved (for example; deletion, insertion, repetition, etc.). If the desired alteration involves deletion or insertion of a site to be altered, one will next select regions of known DNA sequence on either side of the site to be altered which sites can function as primer sites for DNA synthesis. Such embodiments (alteration by deletion or insertion) are exemplified in FIGS. 1 (deletion) and 2 (insertion of a chimeric sequence).

Next, amplifying the quantity of the plasmid vector containing the cloned segment of DNA is required. Following such amplification, the cloned segment of DNA is removed by endonuclease restriction and the cloned segment of DNA is purified from other DNA present following endonuclease restriction.

The methods of the invention each require, as an important step, ligation of the purified cloned segment of DNA to itself. Where one seeks to alter the DNA molecule by insertion or deletion, the purified cloned segment is ligated to itself in such a manner as to create at least a certain population of DNA sequences arranged so that the purified cloned segment of DNA is orientated in a head-to-tail configuration (FIGS. 1 and 2, step 3).

Polymerase chain reaction DNA synthesis is then caused to occur in the population of ligated DNA sequences by hybridizing the sense strand to one of the primers on one side of the site to be altered in combination with hybridizing the anti-sense strand to the other primer on the other side of the site to be altered, both regions acting as primers for DNA synthesis. This specific embodiment is exemplified in FIGS. 1 and 2 at step 4 in each scheme.

In this embodiment, one thereby succeeds in generating at least a certain population of DNA products which include a new DNA fragment in which the two regions of known DNA sequence used as primer sites for DNA synthesis are located on either end of the new DNA fragment (FIGS. 1 and 2, step 5). The new DNA fragment, so constructed, also contains a restriction endonuclease site corresponding to the restriction endonuclease site used initially to remove the original cloned segment of DNA. The endonuclease restriction site is now located in between the two regions of known DNA sequence on either end of the new DNA fragment. Most importantly for the purposes of those embodiments designed to cause deletions or insertions, this new DNA fragment no longer contains the site to be altered.

Having achieved the new DNA fragment deleted for the site to be altered, the method of the present invention allows one, in a specific embodiment, to produce a novel DNA sequence corresponding to the originally cloned segment of DNA but which no longer contains the site to be altered (FIG. 1). First, the new DNA fragment deleted for the site to be altered is purified from other DNA present following DNA synthesis FIG. 1, step 5). Next, the purified new DNA fragment is ligated to itself in such a manner as to create at least a certain population of DNA sequences where the purified new DNA fragment is orientated in a head-to-tail configuration (FIG. 1, step 6).

In those specific embodiments where one seeks to merely achieve a deletion in a given DNA sequence, the population of DNA sequences ligated in a head-to-tail fashion is then treated with the restriction endonuclease capable of restricting the new DNA fragment and releasing the novel DNA sequence (FIG. 1, step 7). This novel DNA sequence no longer contains the site to be altered which was originally present in the cloned segment of DNA. Finally, the novel DNA sequence is purified by methods well known to those of skill in the art and is reinserted into an appropriate plasmid vector. In many cases, the simplest approach will be to merely reinsert the novel DNA sequence back into the vector DNA from which its parent sequence was removed.

In an alternative embodiment which has many similarities to that described for generating a simple deletion, the new DNA fragment (FIG. 2, step 5) may be used to construct a chimeric DNA sequence corresponding to the cloned segment of DNA but now containing a chimeric DNA sequence as an alternative sequence to the site which is to be altered or deleted. In this specific embodiment, one will ligate a chimeric (or new) DNA sequence to the new DNA fragment in such a manner as to produce at least a certain population of chimeric fragments containing the chimeric DNA sequence flanked on either side by copies of the new DNA fragment (FIG. 2, step 6). This is achieved by ligating the chimeric sequence in between two new DNA fragments arranged in a head-to-tail fashion. By so arranging the molecules, the chimeric fragment's orientation corresponds to the orientation of endonuclease restriction sites and the orientation of the regions of known DNA sequence initially used as primers on either side of the site to be altered. The resulting population of chimeric fragments is then restricted with the endonuclease in order to produce the chimeric DNA sequence, purified, and reinserted into an appropriate plasmid vector, as noted above (FIG. 2, steps 7-8). In order to determine that the orientation of the chimeric sequence is identical with that of the original sequence, it is necessary to carry out DNA sequencing on the chimeric sequence.

In certain alternative embodiments, a method is provided for constructing a novel DNA sequence corresponding to a cloned segment of DNA but where the novel DNA sequence is altered to contain a directly repeated site (FIG. 3) or a site repeated in an inverted fashion (FIG. 4). As in the methods exemplified in FIGS. 1 and 2, the methods exemplified in FIGS. 3 and 4 are achieved initially by inserting a cloned segment of DNA into a plasmid vector at a known restriction endonuclease site and, in turn, creating a plasmid vector containing the cloned segment of DNA flanked on either of its sides by two new restriction endonuclease sites corresponding to the known restriction site. The site to be repeated within the cloned segment of DNA is selected and the vector containing the cloned segment of DNA is amplified and, then, removed by endonuclease restriction.

After purifying the cloned segment of DNA from other DNA present following endonuclease restriction, the purified cloned segment of DNA is ligated to itself (FIGS. 3 and 4, step 3). Where one seeks to create a directly repeated sequence, the ligation of the cloned fragment is achieved in such a manner as to create at least a certain population of DNA sequences arranged so that the purified cloned segment of DNA is orientated in a head-to-tail configuration (FIG. 3, step 3). Alternatively, where one seeks to create a repeated sequence in an inverted fashion, the ligation of the cloned fragment to itself is done in a manner to create a tail-to-tail orientation (FIG. 4, step 3).

As distinct from the previous embodiments (as exemplified in FIGS. 1 and 2), in order to cause polymerase chain reaction DNA synthesis to occur in the population of DNA sequences, the primers selected correspond to the outermost termini of the region to be repeated. In other words, as exemplified in FIG. 3, if "5" represents a sequence of DNA one wishes to cause to be directly repeated which comprises 100 base pairs, one would select a primer which corresponds to the first 20 bases of sequence "5", for example, and a primer which corresponds to the last 20 bases of sequence "5." Then, by hybridizing a primer molecule to the sense strand of one of the regions of DNA sequence corresponding to the site to be directly repeated and combining this with hybridization of the other primer molecule to the antisense strand of the other region of DNA sequence corresponding to the site to be directly repeated, a new DNA fragment may be produced. In this manner, both regions at the termini of the site to be directly repeated act as primers for DNA synthesis.

There is generated, thereby, a certain population of DNA products which include a new DNA fragment in which the two regions of DNA sequence used as primer sites for DNA synthesis and which correspond to the termini of the site to be directly repeated are now located on either end of the new DNA fragment (FIGS. 3 and 4, step 5). This new DNA fragment also contains a restriction endonuclease site corresponding to the restriction endonuclease site used to remove the cloned segment of DNA originally. As in the previous embodiments, this endonuclease restriction site is located in between the two regions of DNA sequence used for primer sites for DNA synthesis and corresponds to the site to be directly repeated on either end of the new DNA fragment.

Thereafter, the methods as exemplified in FIGS. 3 and 4 are similar to one another and to the previous embodiments exemplified in FIGS. 1 and 2. Thus, steps are taken to purify the new DNA fragment from other DNA, to ligate the purified new DNA fragment to itself in such a manner as to create at least a certain population of DNA sequences arranged in a head-to-tail configuration, to restrict the resulting population of DNA sequences with the endonuclease capable of restricting the new DNA fragment and releasing thereby the novel DNA sequence now containing the repeated site, to purify the novel DNA sequence, and to reinsert the novel DNA sequence into an appropriate plasmid vector. In so doing, one is able to construct either a molecule containing a directly repeated sequence (FIG. 3, step 7) or a molecule with a sequence repeated in an inverted fashion (FIG. 4, step 7).

Where the methods described supra involve insertion of the resulting novel DNA sequence generated using the techniques of the invention into an appropriate plasmid vector, that vector may be any one of the vectors known to those of skill in the art as an expression vector.

In general, of course, prokaryotes are preferred for the initial cloning of DNA sequences and constructing the vectors useful in the invention. For example, E. coli. HB101 has been shown to be particularly useful. Other microbial strains which may be used include E. coli strains such as E. coli B, and E. coli X 1776 (ATCC No. 31537). These examples are, of course, intended to be illustrative rather than limiting.

Prokaryotes may also be used for expression. The aforementioned strains, as well as E. coli W3110 (F-, lambda-prototrophic, ATCC No. 273325), bacilli such as Bacillus subtilus, or other enterobacteriaceae such as Salmonella typhimurium or Serratia marcesans, and various Pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species and well known to those of skill in the art. The vector pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

Those promoters most commonly used in recombinant DNA construction include the β-lactamase (penicillinase) and lactose promoter systems and a tryptophan (trp) promoter system each of which is well known to those of skill in the art. While these are the most commonly used, other microbial promoters have been discovered and utilized, and details concerning their nucleotide sequences have been published, enabling a skilled worker to ligate them functionally with plasmid vectors.

In addition to prokaryotes, eukaryotic microbes, such as yeast cultures may also be used. Saccharomyces cerevisiase, or common baker's yeast is the most commonly used among eukaryotic microorganisms, although a number of other strains are commonly available. For expression in Saccharomyces, the plasmid YRp7, for example, is commonly used. This plasmid already contains the trpl gene which provides a selection marker for a mutant strain of yeast lacking the ability to grow in tryptophan, for example ATCC No. 44076 or PEP4-1. The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

Whatever expression vector and host cell combination is selected, the methods of the invention may be further utilized to recover a polypeptide encoded by the novel DNA sequence. Methods of recovering such recombinant proteins are well known to those skilled in the art and include lysing of the polypeptide-containing containing cells after an appropriate incubation and growth period, precipitating the polypeptide, chromatographing the crude polypeptide, and concentrating the polypeptide.

BRIEF DESCRIPTION OF THE DRAWINGS

FIG. 1. Schematic of method for constructing deletions within a DNA sequence. DNA sequences A and C represent the regions of known DNA sequence to be used as primers on either side of the site to be altered, shown here as B. The arrows indicate the direction of DNA synthesis along either the sense or anti-sense strand from the given primer site.

FIG. 2. Schematic of method for constructing chimeric DNA sequences. DNA sequences A and C and the arrows are as described in the description to FIG. 1. B' represents the chimeric DNA sequence to be substituted for B.

FIG. 3. Schematic of method used to construct molecule containing a directly repeated sequence. DNA sequence 123456789 represents the regions of known DNA sequence containing the site to be directly repeated, shown here as 5. 5 also provides the sequences (the termini) which are used as the primers in this embodiment. The arrows are as described in the description to FIG. 1.

FIG. 4. Schematic of method used to construct molecule with sequence repeated in an inverted fashion. DNA sequence 123456789 represents the regions of known DNA sequence containing the site to be repeated in an inverted fashion, shown here as 6789. The termini of region 6 are used as the primers in this embodiment. The arrows are as described in the description to FIG. 1.

FIGS. 7A and 7B Gel electroploresis (a) of direct repeat a fragments created when methods of invention used as shown in schematic (B). Kw V is different from V and its location is shown in the computer sequence between −301 to −316.

DESCRIPTION OF THE PREFERRED EMBODIMENTS

Figure 5:
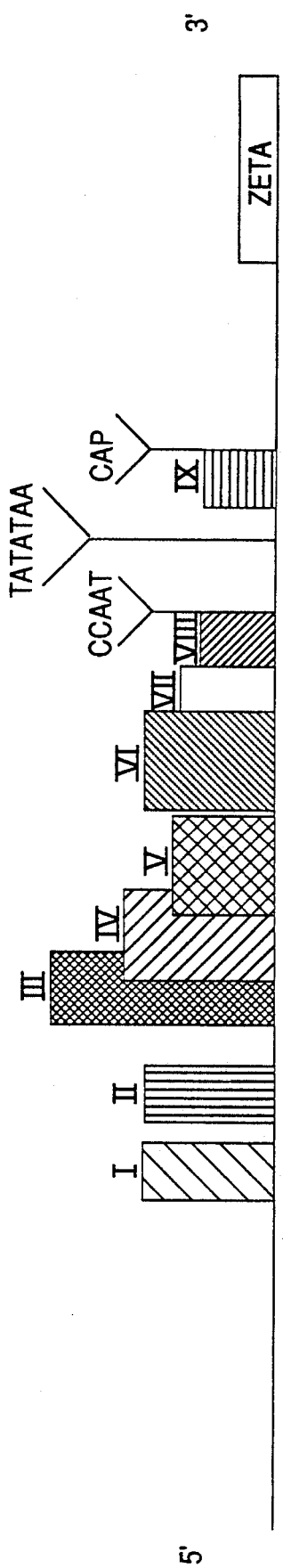
FIG. 5 General characteristics of the promoter region of the Zeta-globin promoter region.

The invention relates to methods for the use of polymerase chain reaction (PCR) technology to construct altered DNA molecules in which DNA sequences have been inserted, deleted or otherwise changed. In particular, the invention relates to a method of altering DNA sequences as small as a single base pair with a high degree of precision.

The methods of the invention are generally applicable to manipulation of any DNA sequence which is amplifiable by PCR. However, and as noted in the background of the invention, there are particular applications in which the present invention will find particular utility. For instance, as noted in Horton, et al. (*Gene* 77:61–68, 1989), generally methods for mutating DNA sequences may be used to construct chimeric genes. Such methods may also be generally applied in order to introduce restriction sites into DNA sequences (Scharf, et al., *Science* 233:1076–1078, 1986). More specifically, manipulation of antibody genes is possible generally using PCR approaches (Orlandi, et al., *Proc.Natl.Acad.-Sci.* 86:3833–3837, 1989). Other applications allow amplification of unknown DNA sequences (Triglia, et al., *Nucl.Acids Res.* 16:8186, 1988; Silver and Keerikatte, *J.Virol.* 63:1924–1928, 1989). Uniquely, however, the present invention also allows facile construction of repeats (both direct and inverse) in DNA sequences.

Specifically, the invention involves the use of a cloned segment of DNA of interest inserted into a plasmid vector (vector DNA) at a known restriction site (for example, EcoRI; note that the restriction enzyme EcoRI is not underlined as conventionally in the following text since underlining in the figures would cause confusion). The DNA of interest contains a site to be altered (for example, B which represents a DNA sequence as small as a single base pair) flanked on either side by regions of known DNA sequence for example, A and C) which sites are capable of functioning as primer sites for PCR amplification by DNA polymerase, (vector DNA) - - - EcoRI . . . A B C . . . EcoRI - - - (vector DNA). [1]

The cloned DNA segment of interest which has been so inserted and which contains the site to be altered (B) flanked by its two primer sites (A and C) is first removed from the plasmid I0 vector by endonuclease restriction (the vector fragment may be saved for later use in conveniently reinserting the altered sequence into a cloning vector at the EcoRI site) at the known restriction site (EcoRI) and the fragment is purified using standard techniques, EcoRI . . . A B C . . . EcoRI. [2]

The purified cloned segment of DNA is then ligated to itself creating at least a certain population of DNA sequences arranged such that the original fragment DNA is orientated in a head-to-tail configuration, EcoRI . . . A B C . . . EcoRI . . . A B C . . . EcoRI. [3]

Using the sense strand of one primer site (C) in combination with the anti-sense strand of the other primer site (A), the head-to-tail DNA sequence is amplified by PCR, EcoRI . . . A B C . . . > . . . EcoRI . . . < . . . A B C . . . EcoRI [4]

A variety of synthetic products are generated by this combination of steps, however, at least some of these products will represent a new DNA fragment in which the two flanking primer sites (C and A) are now located on either end of a DNA sequence containing a single restriction site corresponding to the original restriction site (EcoRI), C . . . EcoRI . . . A. [5]

Most importantly, this PCR-generated DNA fragment is now deleted for the sequence to be altered (B) and contains a restriction site (EcoRI) between the two primer sites. It may be isolated by any of those techniques known well to those of skill in the art for isolating DNA fragments.

Once the PCR-generated sequence deleted for the sequence to be altered (B) is purified, it can be used to create at least two useful derivatives of the original DNA sequence of interest. In one preferred embodiment, the PCR-generated sequence deleted for the target sequence is used to reconstruct the original DNA sequence but which sequence is now lacking the portion corresponding to the sequence to be altered (B). To achieve this result, the fragment is first phosphorylated using a phosphorylating enzyme such as a kinase known well to those of skill in the art. The invention then requires a second round of self-ligation producing at least a certain population of fragments arranged in a head-to-tail configuration, C . . . EcoRI . . . A C . . . EcoRI . . . A [6]

This fragment is then restricted with the restriction endonuclease of choice thereby creating a fragment which may be purified, EcoRI . . . A C . . . EcoRI [7]

and reinserted into an appropriate plasmid vector, (vector DNA) - - - EcoRI . . . A C . . . EcoRI - - - (vector DNA). [8]

Alternatively, the PCR-generated fragment which has been deleted for the target sequence, C . . . EcoRI . . . A. [5]

may be used to reconstruct the original DNA sequence but which sequence now contains a different (chimeric) target sequence. To achieve this result, the invention requires the ligation of the chimeric sequence (B') with the PCR-generated fragment above [5] producing at least a certain population of chimeric fragments containing the chimeric DNA sequence flanked on either side by one of the PCR-generated fragments so that the overall orientation corresponds to the orientation of restriction sites, primer sites and target sequence of the original cloned DNA segment, C . . . EcoRI . . . A B' C . . . EcoRI . . . A. [6']

This fragment is then restricted with the endonuclease of choice thereby generating a fragment which may be purified, EcoRI . . . A B' C . . . EcoRI. [7']

and reinserted into an appropriate plasmid vector, (vector DNA) - - - EcoRI . . . A B' C . . . EcoRI - - - (vector DNA). [8']

Alternatively, the techniques of the invention allow generation of directly repeated DNA sequences within a selected DNA molecule. In this embodiment, the invention also involves the use of a cloned segment of DNA of interest inserted into a plasmid vector (vector DNA) at a known restriction site (for example, EcoRI). The DNA of interest, in this embodiment, contains a site to be directly repeated (for example, "5" which represents a DNA sequence approximately the size of the primer. In this embodiment, there is no requirement for the site to be directly repeated to additionally be flanked on either side by regions of known DNA sequence. Instead, the sequence of the site to be directly repeated itself provides the sequence for the two primer sites for PCR amplification by DNA polymerase, (vector DNA) - - - EcoRI ... 123456789 ... EcoRI
 - - - (vector DNA). [1]

The cloned DNA segment of interest which has been so inserted and which contains the site to be directly repeated (5) and which will function as the two primer sites is first removed from the plasmid vector by endonuclease restriction (as noted above, the vector fragment may be saved for later use in conveniently reinserting the altered sequence into a cloning vector at the EcoRI site) at the known restriction site (EcoRI) and the fragment is purified using standard techniques, EcoRI ... 123456789 ... EcoRI. [2]

The purified cloned segment of DNA is then ligated to itself creating at least a certain population of DNA sequences arranged such that the original fragment DNA is orientated in a head-to-tail configuration, EcoRI ... 23456789 ... EcoRI ... 123456789 ...
EcoRI. [3]

Using the primer capable of hybridizing to the sense strand of one terminus of the site to be repeated (5) in combination with the primer capable of hybridizing to the anti-sense strand of the other terminus of the site to be repeated (5), the head-to-tail DNA sequence is amplified by PCR, EcoRI ... 1234567>89 .. EcoRI .. 12<3456789 ..
. EcoRI. [4]

Specifically, and by way of example, if region 5 were a region representing 100 base pairs of DNA for which a direct repeat was desired,

GAGGAGGAGGAGGAGGAGGA (SEQ. ID NO. 1, POSITIONS 21-40).

A variety of synthetic products are generated by this combination of steps, however, at least some of these products will represent a new DNA fragment in which the two flanking primer sites (the two primer sites representing the termini of region 5) are now located on either end of a DNA sequence containing a single restriction site corresponding to the original restriction site (EcoRI), 56789 ... EcoRI ... 12345. [5]

This PCR-generated DNA fragment now contains two copies of the sequence to be directly repeated (5) and contains a restriction site (EcoRI) between the two copies (the 5's).

Once the PCR-generated sequence above (now containing a duplication of the sequence to be directly repeated—5) is purified, it can be used to create directly repeated derivatives of the original DNA sequence of interest. To achieve this result, the invention requires a second round of self-ligation producing at least a certain population of fragments arranged in a head-to-tail configuration, 56789 ... EcoRI ... 1234556789 ... EcoRI ... 12345. [6]

This fragment is then restricted with the restriction endonuclease of choice thereby creating a fragment which may be purified, EcoRI ... 1234556789 ... EcoRI [7]

and reinserted into an appropriate plasmid vector, (vector DNA) - - - EcoRI ... 1234556789 ... EcoRI
 - - - (vector DNA). [8]

The techniques of the invention also allow generation of two-fold symmetrical DNA sequences within a selected DNA molecule. In this embodiment, the invention again involves the use of a cloned segment of DNA of interest inserted into a plasmid vector (vector DNA) at a known restriction site (for example, EcoRI). The DNA of interest, in this embodiment, contains a segment to be repeated in an inverted fashion (for example, "6789" which represents a DNA sequence as small as a few base pairs). In this embodiment, there is also no requirement for the segment to be repeated in an inverted fashion to additionally be flanked on either side

```
- - - - - - - - - - - - - - - - - - - Region 5 - - - - - - - - - - - - - - - - - - -     (SEQ. ID No. 1)

CATCATCATCATCATCATCA ... 80 bp ... GAGGAGGAGGAGGAGGAGGA
GTAGTAGTAGTAGTAGTAGT ... 80 bp ... CTCCTCCTCCTCCTCCTCCT
``` and primers were constructed according to the method of the invention, two pairs of 20 bp primers which would function properly would be either, CATCATCATCATCATCATCA (SEQ. ID NO. 1, POSITIONS 1-20) and
CTCCTCCTCCTCCTCCTCCT (SEQ. ID NO. 1, POSITIONS 21-40, REVERSE COMPLEMENT)
or
GTAGTAGTAGTAGTAGTAGT (SEQ. ID NO. 1, POSITIONS 1-20, REVERSE COMPLEMENT) and by regions of known DNA sequence. Instead, primers are selected from within the segment so that they represent one or the other terminus of the segment (for example, at either terminus of region 6) to be repeated in an inverted fashion and these termini functions as primer sites for PCR amplification by DNA polymerase, (vector DNA) - - - EcoRI ... 123456789 ... EcoRI
 - - - (vector DNA). [1]

The cloned DNA segment of interest which has been so inserted and which contains the segment to be repeated in an inverted fashion (123456) and the terminus of which (6) will function as two primer sites is first removed from the plasmid vector by endonuclease restriction (the vector fragment may be saved for later use in conveniently reinserting the altered sequence into a cloning vector at the EcoRI site) at the known restriction site (EcoRI) and the fragment is purified using standard techniques, EcoRI ... 123456789 ... EcoRI.  [2]

The purified cloned segment of DNA is then ligated to itself creating at least a certain population of DNA sequences arranged such that the original fragment DNA is orientated in a tail-to-tail configuration, EcoRI ... 123456789 ... EcoRI ... 987654321 ... EcoRI.  [3]

Using the sense strand of one primer site (corresponding to one terminus of region 6) in combination with the anti-sense strand of the other primer site (corresponding to the other terminus of region 6), the tail-to-tail DNA sequence is amplified by PCR, EcoRI ... 12345678>9 ... EcoRI ... 9<87654321 ... EcoRI.  [4]

A variety of synthetic products are generated by this combination of steps, however, at least some of these products will represent a new DNA fragment in which the two flanking primer sites (the two termini of region 6) are now located on either end of a DNA sequence containing a single restriction site corresponding to the original restriction site (EcoRI), 6789 ... EcoRI ... 9876.  [5]

This PCR-generated DNA fragment is now repeated in an inverted fashion and contains a restriction site (EcoRI) between the two repeated segments.

Once the PCR-generated sequence above (now containing a duplication of the sequence to be repeated in an inverted fashion—6789) is purified, it can be used to further create derivatives of the original DNA sequence of interest now repeated in an inverted fashion. To achieve this result, the invention requires a second round of self-ligation producing at least a certain population of fragments arranged in a head-to-head configuration, 6789 ... EcoRI ... 98766789 ... EcoRI ... 9876.  [6]

This fragment is then restricted with the restriction endonuclease of choice thereby creating a fragment which may be purified, EcoRI ... 98766789 ... EcoRI  [7]

and reinserted into an appropriate plasmid vector, (vector DNA) --- EcoRI ... 98766789 ... EcoRI --- (vector DNA).  [8]

The following examples demonstrate the utility of the methods of the invention for altering DNA molecules.

EXAMPLE I

A working example of the invention as it relates to construction of a deleted DNA molecule is provided using the human Zeta-globin promoter region. FIG. 5 illustrates the general characteristics of the promoter region of the zeta-globin DNA gene. It can be seen therein that a series of oligonucleotide primers (I-IX) were derived to be increasingly distant from the CAP site for the Zeta-globin gene sequence. The actual location of each such oligonucleotide primer relative to the zeta-globin CAP site is also shown in FIG. 5 (where the first base pair of the CAP site is numbered +1 and the locations of the oligonucleotide primers are given as negative numbers being 5' of the +1 CAP site). Other aspects important to the promotion activities of the region are indicated on the diagram of the DNA sequence containing the zeta-globin molecule.

In order to initiate the method, the plasmid containing the human Zeta-globin promoter was digested with HindIII and the HindIII DNA digest was electrophoresed on a 2% agarose gel, as generally described in FIG. 1, step 2. The DNA fragment corresponding to a size of 482 base pairs (bp) containing the region of interest was excised from the gel and electroeluted therefrom.

The isolated DNA fragment was next treated with T4 DNA ligase at a concentration of 50 µg/ml DNA and the DNA fragments were allowed to self-ligate at room temperature. This resulted in the generation of a polymer of the DNA fragments joined head-to-tail as generally described in FIG. 1, step 3. This head-to-tail polymer was then used as a template for the following PCR reactions.

PCR amplification was performed with using an automated method in combination with a Perkin-Elmer DNA Thermal Cycler, and as generally described in FIG. 1, step 4. Briefly, 5ng of the end-to-end polymer fragment as prepared above was incubated with a solution containing each of the oligonucleotide primers as described immediately below (1 µM of primer in 100 µl of a 1X PCR buffer consisting of: 10 mM Tris-HCl, pH 8.3; 50 mM KCl; 1.5 mM $MgCl_2$; 0.1% gelatin; 200 µM of each of the four dNTPs). To this mixture was added two units of Taq DNA polymerase and the mixture was heated to 94° C. for 5 minutes, cooled to 55° C. for 2 minutes and then brought to 73° C. for 3 minutes in the first cycle. Then the cycle consisting of: denaturing at 94° C. for 5 minutes; annealing at 55° C. for 2 minutes; and elongating at 73° C. for 7 minutes, was repeated for 30 cycles.

This was accomplished for each of the following pairs of oligonucleotide primers:

| PAIR NO. | SENSE (S) | ANTI-SENSE (AS) |
| --- | --- | --- |
| 1 | VII | I |
| 2 | VII | II |
| 3 | VII | III |
| 4 | VII | IV |
| 5 | VII | V |

Figure 6A:
FIGS. 6A and 6B Gel electrophoresis (A) of deletion fragments created when methods of invention used as shown in schmatic B.
Figure 6B:
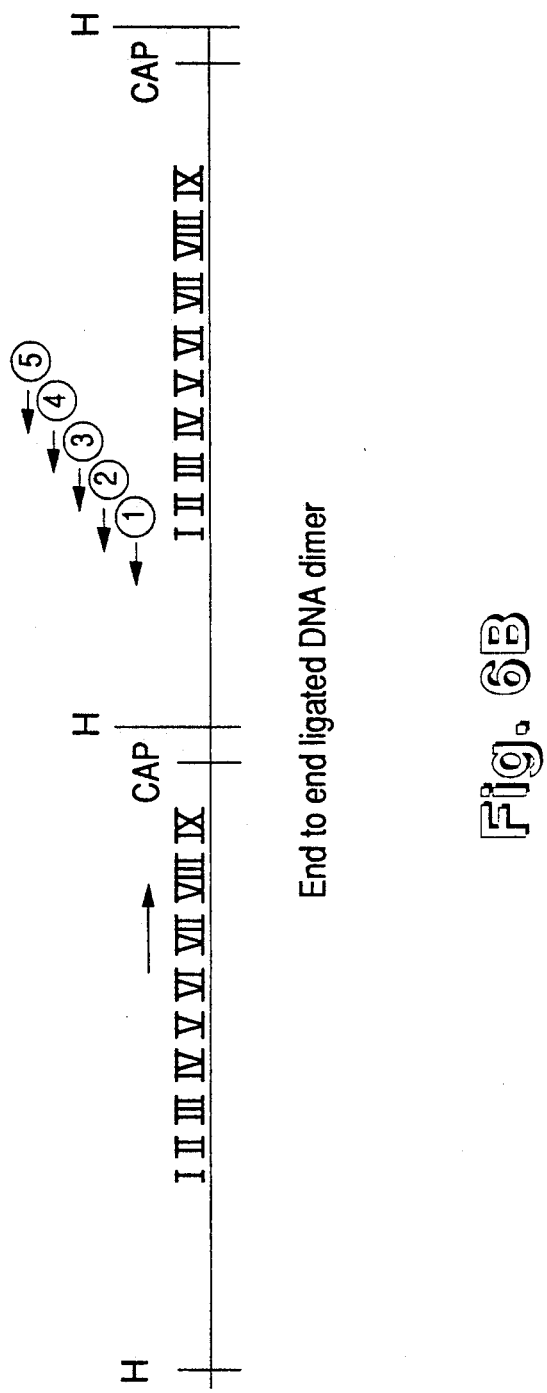

The DNA products thus amplified and deleted were extracted with chloroform, precipitated with ethanol, dissolved in 1X TE (Tris-HCl, EDTA) buffer and electrophoresed on a 2% agarose gel. The 5 resulting DNA fragments were excised and electroeluted in order to isolate the distinctly sized fragments, and as generally described in FIG. 1, step 5. These fragments were then electrophoresed in separate lane on another 2% agarose gel. FIG. 6 is a Polaroid photograph of that gel treated with an ethidium bromide stain and UV illuminated.

As can be seen in FIG. 6, deletions were caused in the DNA fragments as expected from the method resulting in 5 distinctly sized fragments of 321, 342, 386, 423 and 442 bp from the originally sized molecule of 482 bp. Shown also is a diagrammatic representation of the position of the various deletions within the original DNA dimer.

Thus, the 321 bp fragment, for instance then could be represented as:

VII VIII IX CAP Hind . . . I II where roman numerals "VII, VIII, IX, I and II" represent the various primer sites within the promoter sequence still intact in the deleted fragment, "CAP" represents the CAP site prior to the zeta-globin gene, and "Hind" represents the HindIII restriction endonuclease site originally cleaved to generate the fragment. This generates a fragment similar to that in FIG. 1, step 5.

In order to achieve the steps generally outlined in FIG. 1, steps 6-8, for instance, the amplified fragment of pair number 2 (321 bp corresponding to primers VII(S) and II(AS), above) was purified by agarose gel electrophoresis followed by electroelution. The DNA fragment was then kinased using T4 DNA kinase in order to phosphorylate the 5' ends of the DNA fragment and self-ligated using T4 DNA ligase at a concentration of 50 μg/ml DNA. After ligation, the ligated DNA polymers were phenol/chloroform extracted, ethanol precipitated and dissolved in 1X TE buffer. This results in a fragment which may be represented as:

VII VIII IX CAP Hind . . . I II VII VIII IX CAP Hind . . . I II generating a head-to-tail polymer deleted for primer sites II-VI and which fragment in analogous to that seen in FIG. 1, step 6.

The self-ligated DNA was digested again with HindIII and the DNA (approximately 321 bp in size) was subcloned by standard subcloning procedures known well to those of skill in the art into a suitable plasmid vector. This generates a deletion fragment similar to that seen in FIG. 1, steps 7 and 8 and is represented as:

Hind . . . I II VII VIII IX CAP Hind.

The resulting plasmid DNA containing the 321 bp insert now deleted for certain sections of the original promoter. The DNA was isolated from bacteria using the standard alkaline boiling method known well to those of skill in the art and used directly for DNA sequencing by T7 sequenase (United States Biochemical) using an appropriate primer in order to allow read through the junction sequence between original primer sites I and VII. The sequencing primer used was KW V (described below) and the resulting collection of sequencing fragments was electrophoresed on a 5% polyacrylamide gel. The gel was dried and exposed to X-ray sensitive film overnight. The results obtained when the film was developed and the sequence was read show that the DNA sequence through the deleted section of the construct is:

5'-GGGAGGGGTGGGG/AGCTTCT-GATAAGAAACACCA (SEQ. ID NO. 2)

which corresponds to the flipped and complementary 5' end of primer site II(AS) (CCCACCCTCCC) (SEQ. ID NO. 2, POSITIONS 1-12, REVERSE COMPLEMENT) on the one side and corresponds directly to the VII(S) sequence (AGCTTCTGATAA) (SEQ. ID NO. 2, POSITIONS 14-25). This confirms that the junction sequence is exactly as expected from the use of the methods of the invention to create a deleted fragment of the original promoter sequence.

EXAMPLE II

The second example of the methods of the invention concerns creation of direct repeat DNA molecules. The template molecule (analogous to the fragment noted in FIG. 1, step 3) containing the primer sites within the promoter for the zeta-globin gene used in Example I above was used here as well. However, in this case, the PCR treatment had an extended elongation time of 5 minutes rather than 3 minutes during the 30 cycles. This was accomplished in order to insure optimal production of higher molecular weight DNA polymers.

In this example, a primer KW 5 was used in combination with the primers already identified in Example I above. KW 5 is located between −301 and −316 relative to the +1 initiation site 5' of the zeta-globin open reading frame (placing it approximately immediately 5' of original primer site I). The combinations of primers used to construct the direct repeat fragments were as follows:

| PAIR NO. | SENSE (S) | ANTI-SENSE (AS) |
| --- | --- | --- |
| 1 | KW 5 | II |
| 2 | KW 5 | VI |
| 3 | KW 5 | VII |
| 4 | KW 5 | IX |

These primers were used in combination with the template analogous to the fragment noted in FIG. 1, step 3.

The amplified DNA products were electrophoresed on a 2% agarose gel which results are shown in FIG. 7A. As can be seen in that figure, two distinct bands may be observed in each lane above the high background ethidium staining. The lower of the two bands is an artifact produced as a result of the mechanism for generating the direct repeats. The higher of the two distinct bands in each gel can be seen to correspond to the expected size of the direct repeat molecules in each case.

Thus, to reiterate the mechanism of the invention for constructing the KW 5(S)+II(AS) direct repeat as is described in FIG. 3:

1. Insertion of cloned fragment into vector and amplification:

(vector)-Hind . . . I II III IV V VI VII VIII IX . . . Hind-(vector).

2. Restriction of vector DNA containing cloned fragment:

Hind(H) . . . I II III IV V VI VII VIII IX . . . Hind(H)

3. Ligation of restriction fragment to itself, head-to-tail:

H-I II III IV V VI VII VIII IX-H-I II III IV V VI VII VIII IX-H

4. Initiation of polymerase chain reaction at primer sites:

H-I II III>IV V VI VII VIII <IX-H-I II III IV V VI VII VIII IX-H

5. Purification of fragment with two copies of sequence I and II:

I II III IV V VI VII VIII IX ... Hind ... I II

6. Ligation of fragment containing two copies of duplicated sequence to itself, head-to-tail:

I II III IV V VI VII VIII IX-H-I II ... I II III IV V VI VII VIII IX-H-I II

7. Restriction of ligated fragment containing sequences I and II directly repeated:

Hind ... I II/I II III IV V VI VII VIII IX ... Hind without departing from the intended scope of the invention.

For example, sequences as small as a single base pair or a few base pairs may be modified, as noted previously. However, the methods will work equally as well on any size fragment which is amenable to amplification by PCR DNA synthesis. Furthermore, combinations of the methods of the invention may be used to create novel combinations and constructions. For example, a fragment deleted for a certain sequence by the deletion method of the invention may be subsequently used to construct a directly repeated and deleted sequence.

Similarly, although the methods of the invention are most easily practiced with a single, unique restriction site at the termini of the initial substrate molecule, non-identical sites may be used if steps are subsequently taken to insure ligation at these non-identical sites (for example, blunt-ended ligation or attachment of synthetic poly-linkers). All such modifications are intended to be included within the scope of the appended claims.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 40 base pairs
      ( B ) TYPE: nucleic acid
      ( C ) STRANDEDNESS: double
      ( D ) TOPOLOGY: unknown ( v i i ) IMMEDIATE SOURCE:
      ( B ) CLONE: HYPOTHETICAL SEQUENCE ( x i ) SEQUENCE DESCRIPTION: SEQ ID NO:1:

CATCATCATC ATCATCATCA GAGGAGGAGG AGGAGGAGGA     40

( 2 ) INFORMATION FOR SEQ ID NO:2:

( i ) SEQUENCE CHARACTERISTICS:
      ( A ) LENGTH: 34 base pairs
      ( B ) TYPE: nucleic acid
      ( C ) STRANDEDNESS: single
      ( D ) TOPOLOGY: linear ( v i i ) IMMEDIATE SOURCE:
      ( B ) CLONE: ZETA-GLOBIN GENE PROMOTER SEQUENCE ( x i ) SEQUENCE DESCRIPTION: SEQ ID NO:2:

GGGAGGGGTG GGGAGCTTCT GATAAGAAAC ACCA     34

8. Reinsertion of fragment containing sequences I and II directly repeated into vector:

(vector) -H- I II/I II III IV V VI VII VIII IX -H- (vector)

The present invention has been described in terms of particular embodiments proposed to comprise preferred modes for the practice of the invention. It will be appreciated by those of skill in the art that, in light of the present disclosure, numerous modifications and changes can be made in the particular embodiments exemplified

We claim:

1. A method for constructing altered DNA molecules, comprising:
    (a) inserting a cloned segment of DNA into a plasmid vector at a known endonuclease cleavage site and, in turn, creating a new plasmid vector containing the cloned segment of DNA flanked on either of its sides by two new endonuclease cleavage sites corresponding to the known cleavage site;
    (b) selecting a site to be altered within the cloned segment of DNA;

(c) selecting regions of known DNA sequence on either side of the site to be altered which sites can function as primer sites for DNA synthesis;

(d) amplifying the quantity of the plasmid vector containing the cloned segment of DNA;

(e) removing the cloned segment of DNA by endonuclease cleavage;

(f) purifying the cloned segment of DNA from other DNA present following endonuclease cleavage;

(g) ligating the purified cloned segment of DNA to itself in such a manner as to create at least a certain population of DNA sequences arranged so that the purified cloned segment of DNA is orientated in a head-to-tail configuration;

(h) causing polymerase chain reaction DNA synthesis to occur in the population of DNA sequences by hybridizing the sense strand to one of the primers on one side of the site to be altered in combination with hybridizing the anti-sense strand to the other primer on the other side of the site to be altered, both regions acting as primers for DNA synthesis; and, (i) generating at least a certain population of DNA products which include a new DNA fragment in which the two regions of known DNA sequence used as primer sites for DNA synthesis are located on either end of the new DNA fragment, which new DNA fragment also contains an endonuclease cleavage site corresponding to the endonuclease cleavage site used to remove the cloned segment of DNA in step (c), which endonuclease cleavage site is located in between the two regions of known DNA sequence on either end of the new DNA fragment, and which new DNA fragment no longer contains the site to be altered.

2. The method of claim 1 where the new DNA fragment generated in step (i) is used to reconstruct a DNA molecule corresponding to the cloned segment of DNA but which DNA molecule no longer contains the site to be altered which was present in the cloned segment of DNA, comprising;

(a) purifying the new DNA fragment from other DNA present following DNA synthesis;

(b) ligating the purified new DNA fragment to itself in such a manner as to create at least a certain population of DNA molecules such that the purified new DNA fragment is orientated in a head-to-tail configuration;

(c) cleaving the resulting population of DNA sequences with the endonuclease capable of cleaving the new DNA fragment and releasing the DNA molecule no longer containing the site to be altered which was present in the cloned segment of DNA;

(d) purifying the DNA molecule; and, (e) reinserting the DNA molecule into an appropriate plasmid vector.

3. The method of claim 1 where the new DNA fragment is used to construct a chimeric DNA molecule corresponding to the cloned segment of DNA but which chimeric DNA molecule contains an alternative segment to the site which is to be altered, comprising;

(a) ligating the chimeric DNA molecule to the new DNA fragment generated in step (i) in such a manner as to produce at least a certain population of chimeric fragments containing the chimeric DNA molecule flanked on either side by a new DNA fragment so that chimeric fragment's orientation corresponds to the orientation of endonuclease cleavage sites and the orientation of the regions of known DNA sequence on either side of the site to be altered;

(b) cleaving the population of chimeric fragments with the endonuclease in order to produce the chimeric DNA molecule;

(c) purifying the chimeric DNA molecule; and (d) reinserting the chimeric DNA molecule into an appropriate plasmid vector.

4. The method of claim 1 where the new DNA fragment generated in step (i) is used to reconstruct a DNA molecule corresponding to the cloned segment of DNA but which DNA molecule no longer contains the site to be altered which was present in the cloned segment of DNA, comprising;

(a) purifying the new DNA fragment from other DNA present following DNA synthesis;

(b) ligating the purified new DNA fragment to itself in such a manner as to create at least a certain population of DNA molecules such that the purified new DNA fragment is orientated in a head-to-tail configuration;

(c) cleaving the resulting population of DNA molecules with the endonuclease capable of cleaving the new DNA fragment and releasing the DNA molecule no longer containing the site to be altered which was present in the cloned segment of DNA;

(d) purifying the DNA molecule; and, (e) reinserting the DNA molecule into an appropriate plasmid vector, where the appropriate plasmid vector is an expression vector and the DNA molecule generated is operably linked to a promoter region on the expression vector.

5. The method of claim 1 where the new DNA fragment is used to construct a chimeric DNA molecule corresponding to the cloned segment of DNA but which chimeric DNA molecule contains an alternative segment to the site which is to be altered, comprising;

(a) ligating the chimeric DNA molecule to the new DNA fragment generated in step (i) in such a manner as to produce at least a certain population of chimeric fragments containing the chimeric DNA molecule flanked on either side by a new DNA fragment so that chimeric fragment's orientation corresponds to the orientation of endonuclease cleavage sites and the orientation of the regions of known DNA sequence on either side of the site to be altered;

(b) cleaving the population of chimeric fragments with the endonuclease in order to produce the chimeric DNA molecule;

(c) purifying the chimeric DNA molecule; and (d) reinserting the chimeric DNA molecule into an appropriate plasmid vector, where the appropriate plasmid vector is an expression vector and the novel DNA sequence generated is operably linked to a promoter region on the expression vector.

6. A method for constructing a DNA molecule corresponding to a cloned segment of DNA but which DNA sequence no longer contains a site to be altered which was present in the cloned segment of DNA, comprising:

(a) inserting a cloned segment of DNA into a plasmid vector at a known endonuclease cleavage site and, in turn, creating a plasmid vector containing the cloned segment of DNA flanked on either of its sides by two new endonuclease cleavage sites corresponding to the known cleavage site;

(b) selecting a site to be altered within the cloned segment of DNA;

(c) selecting regions of known DNA sequence on either side of the site to be altered which sites can function as primer sites for DNA synthesis;

(d) amplifying the quantity of the plasmid vector containing the cloned segment of DNA;

(e) removing the cloned segment of DNA by endonuclease cleavage;

(f) purifying the cloned segment of DNA from other DNA present following endonuclease cleavage;

(g) ligating the purified cloned segment of DNA to itself in such a manner as to create at least a certain population of DNA molecules arranged so that the purified cloned segment of DNA is orientated in a head-to-tail configuration;

(h) causing polymerase chain reaction DNA synthesis to occur in the population of DNA molecules by utilizing the sense strand of one of the regions of known DNA sequence on one side of the site to be altered in combination with hybridizing the anti-sense strand to the other region of known DNA sequence on the other side of the site to be altered, both regions acting as primers for DNA synthesis;

(i) generating at least a certain population of DNA products which include a new DNA fragment in which the two regions of known DNA sequence used as primer sites for DNA synthesis are located on either end of the new DNA fragment, and which new DNA fragment also contains an endonuclease cleavage site corresponding to the endonuclease cleavage site used to remove the cloned segment of DNA in step (c) above which endonuclease cleavage site is located in between the two regions of known DNA sequence on either end of the new DNA fragment, and which new DNA fragment no longer contains the site to be altered;

(j) purifying the new DNA fragment from other DNA present following DNA synthesis;

(k) ligating the purified new DNA fragment to itself in such a manner as to create at least a certain population of DNA molecules arranged such that the purified new DNA fragment is orientated in a head-to-tail configuration;

(l) cleaving the resulting population of DNA molecules with the endonuclease capable of cleaving the new DNA fragment into two segments and releasing the DNA molecule no longer containing the site to be altered which was present in the cloned segment of DNA;

(m) purifying the DNA molecule; and, (n) reinserting the DNA molecule into an appropriate plasmid vector.

7. A method for constructing a chimeric DNA molecule corresponding to a cloned segment of DNA but which chimeric DNA molecule contains an alternative sequence to a site which is to be altered, comprising;

(a) inserting a cloned segment of DNA into a plasmid vector at a known endonuclease cleavage site and, in turn, creating a new plasmid vector containing the cloned segment of DNA flanked on either of its sides by two new endonuclease cleavage sites corresponding to the known cleavage site;

(b) selecting a site to be altered within the cloned segment of DNA;

(c) selecting regions of known DNA sequence on either side of the site to be altered which sites can function as primer sites for DNA synthesis;

(d) amplifying the quantity of the plasmid vector containing the cloned segment of DNA;

(e) removing the cloned segment of DNA by endonuclease cleavage;

(f) purifying the cloned segment of DNA from other DNA present following endonuclease cleavage;

(g) ligating the purified cloned segment of DNA to itself in such a manner as to create at least a certain population of DNA sequences arranged so that the purified cloned segment of DNA is orientated in a head-to-tail configuration;

(h) causing polymerase chain reaction DNA synthesis to occur in the population of DNA sequences by utilizing the sense strand of one of the regions of known DNA sequence on one side of the site to be altered in combination with the anti-sense strand of the other region of DNA sequence on the other side of the site to be altered, both regions acting as primers for DNA synthesis;

(i) generating at least a certain population of DNA products which include a new DNA fragment in which the two regions of known DNA sequence used as primer sites for DNA synthesis are located on either end of the new DNA fragment, which new DNA fragment also contains an endonuclease cleavage site corresponding to the endonuclease cleavage site used to remove the cloned segment of DNA in step (c), above which endonuclease cleavage site is located in between the two regions of known DNA sequence on either end of the new DNA fragment, and which new DNA fragment no longer contains the site to be altered;

(j) ligating the chimeric DNA molecule to the new DNA fragment in such a manner as to produce at least a certain population of chimeric fragments containing the chimeric DNA molecule flanked on either side by a new DNA fragment so that chimeric fragment's orientation corresponds to the orientation of endonuclease cleavage sites and the orientation of the regions of known DNA sequence on either side of the site to be altered;

(k) cleaving the population of chimeric fragments with the endonuclease in order to produce the chimeric DNA sequence;

(l) purifying the chimeric DNA molecule; and (m) reinserting the chimeric DNA molecule into an appropriate plasmid vector.

8. A method for constructing a DNA molecule corresponding to a cloned segment of DNA but which DNA molecule is altered to contain a directly repeated site which was present in the cloned segment of DNA in only a single copy, comprising:

(a) inserting a cloned segment of DNA into a plasmid vector at a known endonuclease cleavage site and, in turn, creating a new plasmid vector containing the cloned segment of DNA flanked on either of its sides by two new endonuclease cleavage sites corresponding to the known cleavage site;

(b) selecting a site to be altered within the cloned segment of DNA;

(c) amplifying the quantity of the plasmid vector containing the cloned segment of DNA;

(d) removing the cloned segment of DNA by endonuclease cleavage;

(e) purifying the cloned segment of DNA from other DNA present following endonuclease cleavage;

(f) ligating the purified cloned segment of DNA to itself in such a manner as to create at least a certain population of DNA sequences arranged so that the purified cloned segment of DNA is orientated in a head-to-tail configuration;

(g) causing polymerase chain reaction DNA synthesis to occur in the population of DNA sequences by hybridizing a primer molecule to the sense strand of one of the termini of the region of DNA molecule corresponding to the site to be directly repeated in combination with hybridizing a primer molecule to the anti-sense strand of the other terminus of the region of DNA molecule corresponding to the site to be directly repeated, both regions acting as primers for DNA synthesis;

(h) generating at least a certain population of DNA products which include a new DNA fragment in which the two regions of known DNA molecule used as primer sites for DNA synthesis and each of which corresponds to the site to be directly repeated are located on either end of the new DNA fragment, which new DNA fragment also contains an endonuclease cleavage site corresponding to the endonuclease cleavage site used to remove the cloned segment of DNA in step (d) above, which endonuclease cleavage site is located in between the two regions of DNA molecule used for primer sites for DNA synthesis;

(i) purifying the new DNA fragment from other DNA present following DNA synthesis;

(j) ligating the purified new fragment to itself in such a manner as to create at least a certain population of DNA molecules arranged such that the purified new DNA fragment is orientated in a head-to-tail configuration;

(k) cleaving the resulting population of DNA molecules with the endonuclease capable of cleaving the new DNA fragment and releasing the DNA molecule now containing the directly repeated site;

(l) purifying the DNA molecule; and, (m) reinserting the DNA molecule into an appropriate plasmid vector.

9. A method for constructing a DNA molecule corresponding to a cloned segment of DNA but which DNA molecule is altered to contain a site repeated in an inverted fashion which was present in the cloned segment of DNA in only a single copy, comprising:

(a) inserting a cloned segment of DNA into a plasmid vector at a known endonuclease cleavage site and, in turn, creating a new plasmid vector containing the cloned segment of DNA flanked on either of its sides by two new endonuclease cleavage sites corresponding to the known cleavage site;

(b) selecting a site to be repeated in an inverted fashion within the cloned segment of DNA;

(c) amplifying the quantity of the plasmid vector containing the cloned segment of DNA;

(d) removing the cloned segment of DNA by endonuclease cleavage;

(e) purifying the cloned segment of DNA from other DNA present following endonuclease cleavage;

(f) ligating the purified cloned segment of DNA to itself in such a manner as to create at least a certain population of DNA molecules arranged so that the purified cloned segment of DNA is orientated in a head-to-tail configuration;

(g) causing polymerase chain reaction DNA synthesis to occur in the population of DNA molecules by hybridizing a primer molecule to the sense strand of one of the termini of the region of DNA molecule corresponding to the site to be repeated in an inverted fashion in combination with hybridizing a primer molecule to the anti-sense strand of the other terminus of the region of DNA molecule corresponding to the site to be repeated in an inverted fashion, both regions acting as primers for DNA synthesis;

(h) generating at least a certain population of DNA products which include a new DNA fragment in which the two regions of known DNA molecule used as primer sites for DNA synthesis and each of which corresponds to the site to be repeated in an inverted fashion are located on either end of the new DNA fragment, which new DNA fragment also contains an endonuclease cleavage site corresponding to the endonuclease cleavage site used to remove the cloned segment of DNA in step (d) above, which endonuclease cleavage site is located in between the two regions of DNA sequence used for primer sites for DNA synthesis;

(i) purifying the new DNA fragment from other DNA present following DNA synthesis;

(j) ligating the purified new fragment to itself in such a manner as to create at least a certain population of DNA molecules arranged such that the purified new DNA fragment is orientated in a head-to-tail configuration;

(k) cleaving the resulting population of DNA molecules with the endonuclease capable of cleaving the new DNA fragment and releasing the DNA molecule now containing the site duplicated in an inverted fashion;

(l) purifying the DNA molecule; and, (m) reinserting the DNA molecule into an appropriate plasmid vector.

10. A method for constructing altered DNA molecules, comprising:

(a) inserting a cloned segment of DNA into a plasmid vector at a known endonuclease cleavage site and, in turn, creating a new plasmid vector containing the cloned segment of DNA flanked on either of its sides by two new endonuclease cleavage sites corresponding to the known cleavage site;

(b) selecting a site to be altered within the cloned segment of DNA, where the site to be altered comprises a single base pair;

(c) selecting regions of known DNA sequence on either side of the site to be altered which sites can function as primer sites for DNA synthesis;

(d) amplifying the quantity of the plasmid vector containing the cloned segment of DNA;

(e) removing the cloned segment of DNA by endonuclease cleavage;

(f) purifying the cloned segment of DNA from other DNA present following endonuclease cleavage;

(g) ligating the purified cloned segment of DNA to itself in such a manner as to create at least a certain population of DNA molecules arranged so that the purified cloned segment of DNA is orientated in a head-to-tail configuration;

(h) causing polymerase chain reaction DNA synthesis to occur in the population of DNA sequences by hybridizing the sense strand to one of the primers on one side of the site to be altered in combination with hybridizing the anti-sense strand to the other primer on the other side of the site to be altered, both regions acting as primers for DNA synthesis; and, (i) generating at least a certain population of DNA products which include a new DNA fragment in which the two regions of known DNA sequence used as primer sites for DNA synthesis are located on either end of the new DNA fragment, which new DNA fragment also contains an endonuclease cleavage site corresponding to the endonuclease cleavage site used to remove the cloned segment of DNA in step (c), which endonuclease cleavage site is located in between the two regions of known DNA sequence on either end of the new DNA fragment, and which new DNA fragment no longer contains the site to be altered.

11. A method for constructing a DNA molecule corresponding to a cloned segment of DNA but which DNA molecule no longer contains a site to be altered which was present in the cloned segment of DNA, comprising;

(a) inserting a cloned segment of DNA into a plasmid vector at a known endonuclease cleavage site and, in turn, creating a plasmid vector containing the cloned segment of DNA flanked on either of its sides by two new endonuclease cleavage sites corresponding to the known cleavage site;

(b) selecting a site to be altered within the cloned segment of DNA;

(c) selecting regions of known DNA sequence on either side of the site to be altered which sites can function as primer sites for DNA synthesis;

(d) amplifying the quantity of the plasmid vector containing the cloned segment of DNA;

(e) removing the cloned segment of DNA by endonuclease cleavage;

(f) purifying the cloned segment of DNA from other DNA present following endonuclease cleavage;

(g) ligating the purified cloned segment of DNA to itself in such a manner as to create at least a certain population of DNA molecules arranged so that the purified cloned segment of DNA is orientated in a head-to-tail configuration;

(h) causing polymerase chain reaction DNA synthesis to occur in the population of DNA sequences by utilizing the sense strand of one of the regions of known DNA sequence on one side of the site to be altered in combination with hybridizing the anti-sense strand of the other region of known DNA sequence on the other side of the site to be altered, both regions acting as primers for DNA synthesis;

(i) generating at least a certain population of DNA products which include a new DNA fragment in which the two regions of known DNA sequence used as primer sites for DNA synthesis are located on either end of the new DNA fragment, and which new DNA fragment also contains an endonuclease cleavage site corresponding to the endonuclease cleavage site used to remove the cloned segment of DNA in step (c), above which endonuclease cleavage site is located in between the two regions of known DNA sequence on either end of the new DNA fragment, and which new DNA fragment no longer contains the site to be altered;

(j) purifying the new DNA fragment from other DNA present following DNA synthesis;

(k) ligating the purified new DNA fragment to itself in such a manner as to create at least a certain population of DNA molecules arranged such that the purified new DNA fragment is orientated in a head-to-tail configuration;

(l) cleaving the resulting population of DNA molecules with the endonuclease capable of cleaving the new DNA fragment into two segments and releasing the DNA molecule no longer containing the site to be altered which was present in the cloned segment of DNA;

(m) purifying the DNA molecule; and, (n) reinserting the DNA molecule into an appropriate plasmid vector, where the appropriate plasmid vector is an expression vector and the DNA molecule generated is operably linked to a promoter region on the expression vector.

12. A method for constructing a chimeric DNA molecule corresponding to a cloned segment of DNA but which chimeric DNA molecule contains an alternative segment to a site which is to be altered, comprising;

(a) inserting a cloned segment of DNA into a plasmid vector at a known endonuclease cleavage site and, in turn, creating a plasmid vector containing the cloned segment of DNA flanked on either of its sides by two new endonuclease cleavage sites corresponding to the known cleavage site;

(b) selecting a site to be altered within the cloned segment of DNA;

(c) selecting regions of known DNA sequence on either side of the site to be altered which sites can function as primer sites for DNA synthesis;

(d) amplifying the quantity of the plasmid vector containing the cloned segment of DNA;

(e) removing the cloned segment of DNA by endonuclease cleavage;

(f) purifying the cloned segment of DNA from other DNA present following endonuclease cleavage;

(g) ligating the purified cloned segment of DNA to itself in such a manner as to create at least a certain population of DNA sequences arranged so that the purified cloned segment of DNA is orientated in a head-to-tail configuration;

(h) causing polymerase chain reaction DNA synthesis to occur in the population of DNA molecules by utilizing the sense strand of one of the regions of known DNA sequence on one side of the site to be altered in combination with the anti-sense strand of the other region of known DNA sequence on the other side of the site to be altered, both regions acting as primers for DNA synthesis;

(i) generating at least a certain population of DNA products which include a new DNA fragment in which the two regions of known DNA sequence used as primer sites for DNA synthesis are located on either end of the new DNA fragment, and which new DNA fragment also contains an endonuclease cleavage site corresponding to the endonuclease cleavage site used to remove the cloned segment of DNA in step (c), which endonuclease cleavage site is located in between the two regions of known DNA sequence on either end of the new DNA fragment, and which new DNA fragment no longer contains the site to be altered;

(j) ligating the chimeric DNA molecule to the new DNA fragment in such a manner as to produce at least a certain population of chimeric fragments containing the chimeric DNA molecule flanked on either side by a new DNA fragment so that chimeric fragment's orientation corresponds to the orientation of endonuclease cleavage sites and the orientation of the regions of known DNA sequence on either side of the site to be altered;

(k) cleaving the population of chimeric fragments with the endonuclease in order to produce the chimeric DNA molecule;

(l) purifying the chimeric DNA molecule; and (m) reinserting the chimeric DNA molecule into an appropriate plasmid vector, where the appropriate plasmid vector is an expression vector and the DNA molecule generated is operably linked to a promoter region on the expression vector.

13. A method for constructing a DNA molecule corresponding to a cloned segment of DNA but which DNA molecule is altered to contain a directly repeated site which was present in the cloned segment of DNA in only a single copy, comprising;

(a) inserting a cloned segment of DNA into a plasmid vector at a known endonuclease cleavage site and, in turn, creating a new plasmid vector containing the cloned segment of DNA flanked on either of its sides by two new endonuclease cleavage sites corresponding to the known cleavage site;

(b) selecting a site to be directly repeated within the cloned segment of DNA;

(c) amplifying the quantity of the plasmid vector containing the cloned segment of DNA;

(d) removing the cloned segment of DNA by endonuclease cleavage;

(e) purifying the cloned segment of DNA from other DNA present following endonuclease cleavage;

(f) ligating the purified cloned segment of DNA to itself in such a manner as to create at least a certain population of DNA molecules arranged so that the purified cloned segment of DNA is orientated in a head-to-tail configuration;

(g) causing polymerase chain reaction DNA synthesis to occur in the population of DNA molecules by hybridizing a primer molecule to the sense strand of one of the termini of the region of DNA molecule corresponding to the site to be directly repeated in combination with hybridizing a primer molecule to the anti-sense strand of the other terminus of the region of DNA molecule corresponding to the site to be directly repeated, both regions acting as primers for DNA synthesis;

(h) generating at least a certain population of DNA products which include a new DNA fragment in which the two regions of DNA molecule used as primer sites for DNA synthesis and each of which corresponds to the site to be directly repeated are located on either end of the new DNA fragment, which new DNA fragment also contains an endonuclease cleavage site corresponding to the endonuclease cleavage site used to remove the cloned segment of DNA in step (d) above, which endonuclease cleavage site is located in between the two regions of DNA molecule used for primer sites for DNA synthesis;

(i) purifying the new DNA fragment from other DNA present following DNA synthesis;

(j) ligating the purified new DNA fragment to itself in such a manner as to create at least a certain population of DNA molecules arranged such that the purified new DNA fragment is orientated in a head-to-tail configuration;

(k) cleaving the resulting population of DNA molecules with the endonuclease capable of cleaving the new DNA fragment and releasing the DNA molecule now containing the directly repeated site;

(l) purifying the DNA molecule; and, (m) reinserting the DNA molecule into an appropriate plasmid vector, where the appropriate plasmid vector is an expression vector and the DNA molecule generated is operably linked to a promoter region on the expression vector.

14. A method for constructing a DNA molecule corresponding to a cloned segment of DNA but which DNA molecule is altered to contain a site repeated in an inverted fashion which was present in the cloned segment of DNA in only a single copy, comprising:

(a) inserting a cloned segment of DNA into a plasmid vector at a known endonuclease cleavage site and, in turn, creating a plasmid vector containing the cloned segment of DNA flanked on either of its sides by two new endonuclease cleavage sites corresponding to the known cleavage site;

(b) selecting a site to be repeated in an inverted fashion within the cloned segment of DNA;

(c) amplifying the quantity of the plasmid vector containing the cloned segment of DNA;

(d) removing the cloned segment of DNA by endonuclease cleavage;

(e) purifying the cloned segment of DNA from other DNA present following endonuclease cleavage;

(f) ligating the purified cloned segment of DNA to itself in such a manner as to create at least a certain population of DNA molecules arranged so that the purified cloned segment of DNA is orientated in a head-to-tail configuration;

(g) causing polymerase chain reaction DNA synthesis to occur in the population of DNA molecules by hybridizing a primer molecule to the sense strand of one of the termini of the region of DNA sequence corresponding to the site to be repeated in an inverted fashion in combination with hybridizing a primer molecule to the anti-sense strand of the other terminus of the region of DNA molecule corresponding to the site to be repeated in an inverted fashion, both regions acting as primers for DNA synthesis;

(h) generating at least a certain population of DNA products which include a new DNA fragment in which the two regions of DNA sequence used as primer sites for DNA synthesis and each of which corresponds to the site to be repeated in an inverted fashion are located on either end of the new DNA fragment, which new DNA fragment also contains an endonuclease cleavage site corresponding to the endonuclease cleavage site used to remove the cloned segment of DNA in step (d) above, which endonuclease cleavage site is located in between the two regions of DNA molecule used for primer sites for DNA synthesis;

(i) purifying the new DNA fragment from other DNA present following DNA synthesis;

(j) ligating the purified new DNA fragment to itself in such a manner as to create at least a certain population of DNA molecules arranged such that the purified new DNA fragment is orientated in a head-to-tail configuration;

(k) cleaving the resulting population of DNA molecules with the endonuclease capable of cleaving the new DNA fragment and releasing the DNA sequence now containing the site duplicated in an inverted fashion;

(l) purifying the DNA molecule; and, (m) reinserting the DNA molecule into an appropriate plasmid vector, where the appropriate plasmid vector is an expression vector and the novel DNA molecule generated is operably linked to a promoter region on the expression vector.

* * * * *